(12) United States Patent
Mark et al.

(10) Patent No.: US 12,342,991 B2
(45) Date of Patent: Jul. 1, 2025

(54) SURGICAL ACCESS DEVICE WITH INTEGRATED ILLUMINATION

(71) Applicant: Nico Corporation, Indianapolis, IN (US)

(72) Inventors: Joseph L. Mark, Indianapolis, IN (US); Kristin L. Murphy, Novi, MI (US)

(73) Assignee: NICO Corporation, Indianapolis, IN (US)

( * ) Notice: Subject to any disclaimer, the term of this patent is extended or adjusted under 35 U.S.C. 154(b) by 454 days.

(21) Appl. No.: 17/630,954

(22) PCT Filed: Jul. 28, 2020

(86) PCT No.: PCT/US2020/043817
§ 371 (c)(1),
(2) Date: Jan. 28, 2022

(87) PCT Pub. No.: WO2021/021777
PCT Pub. Date: Feb. 4, 2021

(65) Prior Publication Data
US 2022/0273167 A1 Sep. 1, 2022

Related U.S. Application Data

(60) Provisional application No. 62/881,029, filed on Jul. 31, 2019.

(51) Int. Cl.
*A61B 17/34* (2006.01)
*A61B 1/06* (2006.01)
*A61B 90/30* (2016.01)

(52) U.S. Cl.
CPC ........ *A61B 1/0676* (2013.01); *A61B 17/3421* (2013.01); *A61B 2090/309* (2016.02)

(58) Field of Classification Search
CPC ..... A61B 90/30; A61B 2090/309; A61B 1/06; A61B 1/0607; A61B 1/0615; A61B 17/3421
See application file for complete search history.

(56) References Cited

U.S. PATENT DOCUMENTS

| | | | |
|---|---|---|---|
| 8,430,813 B2* | 4/2013 | Selover | A61B 1/0607 600/245 |
| 9,161,820 B2 | 10/2015 | Mark et al. | |
| 2006/0224045 A1* | 10/2006 | Whipple | A61B 90/30 600/245 |
| 2007/0100211 A1* | 5/2007 | Selover | A61B 17/02 600/199 |
| 2012/0265022 A1* | 10/2012 | Menn | A61B 17/3421 600/245 |
| 2014/0213851 A1 | 7/2014 | Vayser et al. | |

(Continued)

*Primary Examiner* — Eduardo C Robert
*Assistant Examiner* — Michelle C Green
(74) *Attorney, Agent, or Firm* — Howard & Howard Attorneys PLLC (57) ABSTRACT

An outer sheath used with a surgical access assembly is disclosed. The outer sheath includes a proximal end, a distal end and a body portion therebetween. The proximal end defines a first opening. The distal end is disposed opposite the proximal end and defines a second opening. The body portion includes at least one slot formed therein. At least one light source is retained within the slot, adjacent the proximal end.

20 Claims, 8 Drawing Sheets

(56) References Cited

U.S. PATENT DOCUMENTS

2015/0098216 A1    4/2015  Hatzilias et al.
2015/0374222 A1*  12/2015  Mark ...................... A61B 1/32
                                                                               600/204
2017/0215715 A1    8/2017  Harrah et al.

* cited by examiner

SURGICAL ACCESS DEVICE WITH INTEGRATED ILLUMINATION

CROSS-REFERENCE TO RELATED APPLICATIONS

This application is the U.S. National Phase of PCT Application No. PCT/US2020/043817 filed on Jul. 28, 2020, which claims the benefit of U.S. provisional application Ser. No. 62/881,029, filed on Jul. 31, 2019, the disclosures of which are hereby incorporated in their entirety by reference herein.

FIELD

The present disclosure relates generally to a surgical access device with illumination.

BACKGROUND

This section provides background information related to the present disclosure and is not necessarily prior art.

Diagnosis and treatment of conditions affecting the brain are among the most difficult and complex problems that face the medical profession. The brain is a complex and delicate soft multi-component tissue structure that controls bodily functions through a complex neural network connected to the rest of the body through the spinal cord. The brain and spinal cord are contained within and protected by significant bony structures, e.g., the skull and the spine. Given the difficulty of accessing the brain through the hard bony protective skull and the delicate network and complex interactions that form the neural communication network contained within the brain that define the human body's ability to carry on its functions of speech, sight, hearing, functional mobility, reasoning, emotions, respiration and other metabolic functions, the diagnosis and treatment of brain disorders presents unique challenges not encountered elsewhere in the body.

For example, abnormalities such as intracranial cerebral hematomas (ICH), abscesses, Glioblastomas (GB) and metastases (mets) manifest themselves in the intraparenchymal subcortical space (i.e., the white matter) of the brain are particularly challenging to access, let alone treat. The ventricles of the brain contain eloquent communication structures (neural network) which are located in the subcortical space, called fiber tracts and fascicles. Thus, traditionally, unless the ICH, GB, and/or mets where considered anything but "superficial," such conditions have been considered inoperable, simply because getting to the abnormality ICH, GB and/or mets are considered just as damaging as letting the condition take its course. Similarly, tissue abnormalities such as tumors, cysts and fibrous membrane growths which manifest within the intraventricular space of the brain are considered challenging to safely access and often inoperable, due to their locations within the brain.

In order to assist in diagnosis and subsequent treatment of brain disorders, clear, accurate imaging of brain tissue through the skull is required. In recent years significant advances have been made in imaging technology, including stereotactic X-ray imaging, Computerized Axial Tomography (CAT), Computerized Tomographic Angiography (CTA), Position Emission Tomography (PET) and Magnetic Resonance Imaging (MRI), Diffusion Tensor Imaging (DTI) and Navigation systems (instrument position tracking systems). These imaging devices and techniques permit the surgeon to observe conditions within the brain in a non-invasive manner without opening the skull, as well as provide a map of critical structures surrounding an area of interest, including structures such as blood vessels, membranes, tumor margins, cranial nerves, including fiber tracts and fascicles. If an abnormality is identified through the use of one or more imaging modalities and/or techniques, it may be necessary or desirable to biopsy or remove the abnormality.

Once a course of action has been determined based upon one or more imaging techniques, a surgical treatment may be necessary or desired. In order to operate surgically on the brain, access must be obtained through the skull and delicate brain tissue containing blood vessels and nerves that can be adversely affected by even slight disturbances. Therefore, great care must be taken in operating within the brain so as not to disturb delicate blood vessels and nerves to prevent adverse consequences resulting from a surgical intervention.

Traditionally, accessing abnormalities which manifest in deeper spaces within the brain has meant a need for a surgery that creates a highly invasive approach. In some instances, in order to obtain access to target tissue, a substantial portion of the skull is removed and entire sections of the brain are retracted to obtain access. For example, surgical brain retractors are used to pull apart or spread delicate brain tissue, which can produce transient and/or permanent deficits. In some instances, a complication known as "retraction injury" may occur due to use of brain retractors. Of course, such techniques are not appropriate for all situations, and not all patients are able to tolerate and recover from such invasive techniques.

It is also known to access certain portions of the brain by creating a burr hole craniotomy, but only limited surgical techniques may be performed through such smaller openings. In addition, some techniques have been developed to enter through the nasal passages, opening an access hole through the bone to remove skull-based tumors, for example, in the area of the pituitary.

A significant advance in brain surgery is stereotactic surgery involving a stereotactic frame correlated to stereotactic X-ray images to guide a navigational system probe or other surgical instrument through an opening formed in the skull through brain tissue to a target lesion or other body. A related advance is frameless image guidance, in which an image of the surgical instrument is superimposed on a pre-operative image to demonstrate the location of the instrument to the surgeon and trajectory of further movement of the probe or instrument.

One issue with surgical access systems is visibility. Typically when employing an access system in a surgical procedure, it is often like operating in a poorly lit tunnel. To provide illumination, it is known to employ a separate lighting apparatus to deliver light to illuminate the surgical corridor. Known arrangements include the use of a microscope or endoscope. However, an issue that arises with the use of such devices is the need to position the lighting device back and away from the surgical area to provide a working space for the surgical equipment used during the procedure. More specifically, the volume of light is greatly reduced or even lost as the equipment is placed further back, providing less light to actually illuminate the surgical corridor. Furthermore, placement of an additional device into a working channel can crowd the work space within the working channel leading to operator fatigue in manipulating the devices in the small space. Moreover, instrument management also is an issue in that there is a need for a mechanism to hold the illumination device while manipulating other surgical devices. Further, in some instances, positioning a light source in proximity to tissue in the body, especially including the brain, may generate undesirable heat, causing tissue damage.

With more devices being used, another issue arises concerning locating wires to provide power to the light source. Positioning wires within the working channel to illuminate a light source inside the sheath may take up a significant amount of work space within the working channel and/or interfere with surgical tool use within the working channel. In addition, the cords can adversely occlude visibility through the corridor. Further, there is also a need to be cautious when locating wires on the outside of the working channel as the wires need to be separately managed when positioning the access sheath within the body. For example, wires must be kept away from making contact with brain tissue, as well as insuring that proper surgical protocols are being managed in the surgical field.

Notwithstanding the foregoing advances, there remains a need for improved surgical techniques and apparatuses for operating on brain tissue, including providing improved visibility, while minimizing trauma.

SUMMARY

This section provides a general summary of the disclosure, and is not a comprehensive disclosure of its full scope or all of its features.

In one exemplary arrangement, an outer sheath having integrated illumination that may be used with a surgical access assembly is disclosed. The outer sheath includes a proximal end, a distal end and a body portion therebetween. The proximal end defines a first opening. The distal end is disposed opposite the proximal end and defines a second opening. The body portion includes at least one slot formed therein. The at least one slot retains at least one light source adjacent the proximal end.

Aspects of the disclosure may include one or more of the following optional features. In some aspects, the at least one light source is an LED light element. In another aspect, the at least one LED light element is inset within the slot so as to be positioned inwardly from an inner surface of the body portion of the outer sheath. Alternatively, the light source may be positioned to be flush with an inner surface of the outer sheath.

In another aspect of the disclosure, the light source is defined by an illumination end and wherein the illumination end is oriented toward the passageway. Alternatively, the illumination end is oriented downward, either toward the thickness of the outer sheath or into a channel disposed within the thickness of the outer sheath.

In another aspect of the disclosure, operatively connected to a power source by a wired connection and wherein the wired connection orients wires external to the body portion.

In another aspect of the disclosure, at least one segment of the body portion is frosted.

In another aspect of the disclosure, the body portion is defined by an outer surface and an inner surface. The inner surface is spaced from the outer surface to define an annular channel therebetween. The body portion may further include one or more apertures. The apertures extend through the inner surface of the body portion to provide communication between the annular channel and the passageway within the body portion.

In yet another aspect, the light source is oriented to deliver light through the annular channel. Light may be delivered to an inner lumen of the body portion through the apertures.

In yet another aspect, the body portion further includes at least one light element located adjacent the distal end.

In yet another aspect, the slot is formed as an annular notch. Further, the notch may be configured to receive a light source that is configured as an annular ring having a plurality of lights therein.

Another exemplary arrangement of the disclosure provides an outer sheath for a surgical access assembly. The outer sheath includes a proximal end, a distal end and a hollow body portion therebetween. The proximal end defines a first opening. The distal end is positioned opposite the proximal end and defines a second opening. The hollow body portion defines a lumen therethrough. The body portion is further defined by an outside surface and an inside surface. A grip portion is disposed around the first opening and including a mounting flange. The outer sheath further includes a transition section extending between the grip portion and the body portion, the transition section having a first end connected to the grip portion and a second end connected to the proximal end. The mounting flange includes at least one light element mounted there therein and oriented downward to illuminate the lumen.

This aspect may include one or more of the following optional features. In one aspect, the light element is oriented toward the thickness of the body portion that is defined by the inner and outer surfaces. In yet another aspect, at least one channel is formed between the outside surface and the inside surface and the inside surface may include at least one aperture that is in communication with the at least one channel.

In another aspect, the transition section includes at least one opening defined on an inside surface of the transition section. The opening is aligned with the light element.

In yet another aspect, the body portion further includes a plurality of channels between the outside surface and the inside surface.

In another aspect, the at least one light element is an LED light.

In another aspect, at least one segment of the hollow body portion is frosted.

In yet another aspect, the body portion further includes at least one light element located adjacent the distal end.

Another exemplary arrangement of the disclosure provides an outer sheath for a surgical access assembly. The outer sheath includes a proximal end, a distal end and a body portion therebetween. The proximal end defines a first opening. The distal end is disposed opposite the proximal end and defines a second opening. The body portion includes at least one slot form therein. The at least one slot retains at least one light source. The body portion also includes a printed circuit board. The printed circuit board is disposed on an inner surface of the body portion. The printed circuit board extends from the proximal end and is spaced apart from the distal end. The printed circuit board is electrically connected to the at least one light source and facilitates power to the light source.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected configurations and not all possible implementations, and are not intended to limit the scope of the present disclosure.

Exemplary embodiments of the present disclosure will now be described in greater detail with reference to the attached figures, in which.

Corresponding reference numerals indicate corresponding parts throughout the drawings.

DETAILED DESCRIPTION

Referring now to the discussion that follows and also to the drawings, illustrative approaches to the disclosed assemblies are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Described herein is surgical access assembly and various components for use in same. The components disclosed herein provide surgeons with an enhanced ability to minimize trauma to the patient, while providing efficient improved minimally invasive surgical techniques, such as, for example, during intracranial surgical techniques.

Figure 1:
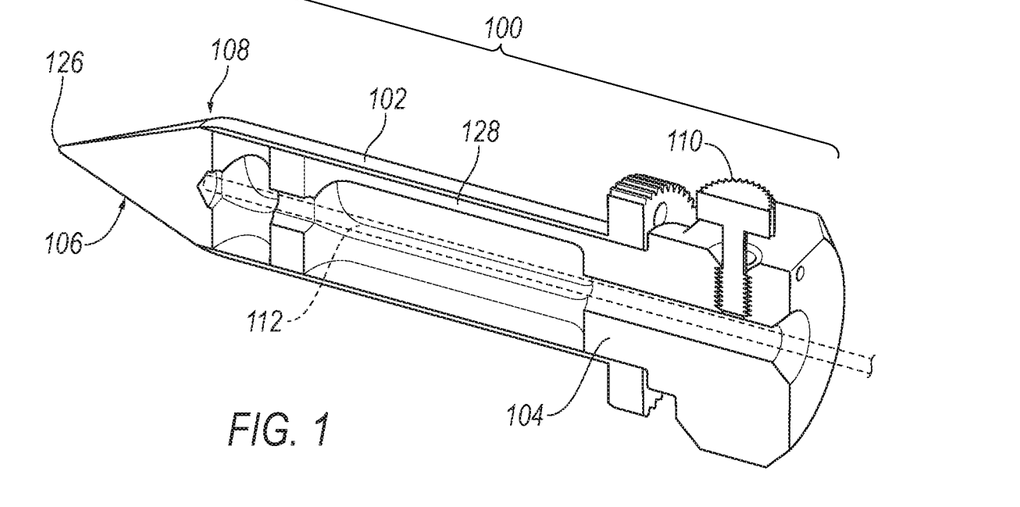
FIG. 1 is a perspective cross-sectional view of an exemplary arrangement of a prior art surgical access assembly.

Referring to FIG. 1, an exemplary arrangement of a surgical access assembly 100 is shown. In one exemplary arrangement, surgical access assembly 100 includes a hollow outer sheath 102 and a selectively removable obturator 104. As seen in FIG. 1, obturator 104 is configured with a length that is longer than a length of the outer sheath 102 such that a distal end 106 of obturator 104 protrudes a predetermined distance from a distal end 108 of outer sheath 102. A navigation system may also be provided. In one exemplary arrangement, the navigation system includes locking member 110, which may be configured to operatively retain a separate navigation member 112 (shown in phantom) within obturator 104. An example of the surgical access assembly 100 may be found in commonly owned U.S. Pat. No. 9,161,820, the contents of which are incorporated by reference in its entirety.

Figure 2:
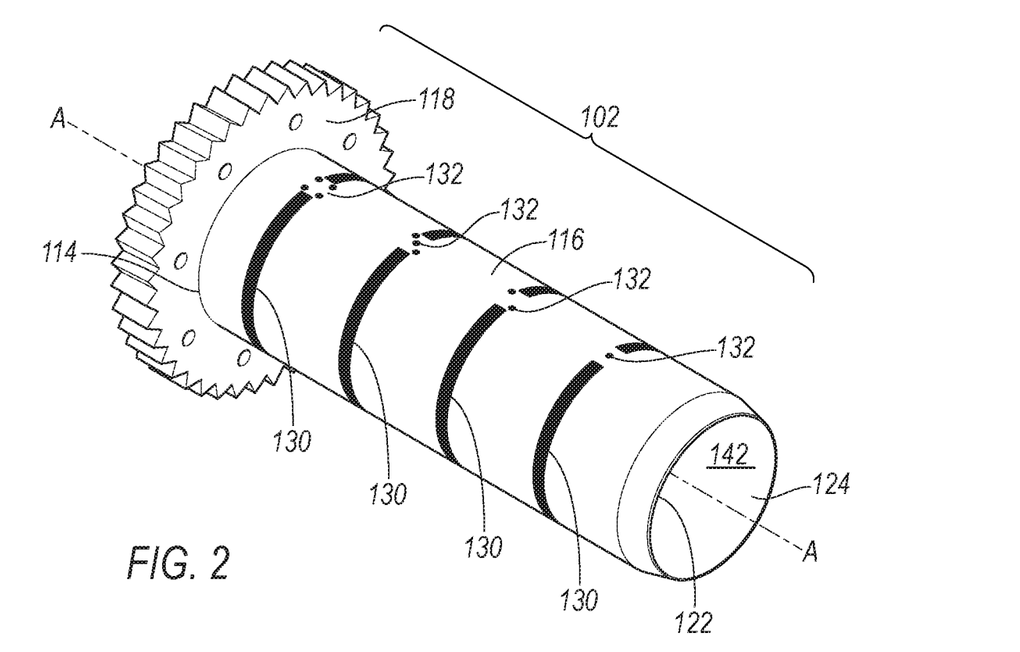
FIG. 2 is a perspective view of an outer sheath of the surgical access assembly of FIG. 1.

Referring now to FIG. 2, outer sheath 102 will be described in greater detail. Outer sheath 102 is defined by the distal end 108 and a proximal end 114 and has a generally hollow body portion 116 therebetween. A grip portion 118 may be provided at the proximal end 114. In one exemplary arrangement, grip portion 118 is a ring, as illustrated in the drawings. However, it is understood that grip portion 118 need not be a ring and may take any shape. In some arrangements, grip portion 118 is unitary with the body portion 116 at proximal end 114, and is formed as one part therewith. In other arrangements, grip portion 118 is a separate element fixedly secured to body portion 116 at proximal end 114.

In one exemplary arrangement, body portion 116 may be constructed of a clear biocompatible material that permits viewing of normal tissue, abnormal tissue, as well as critical structures that are disposed outside of body portion 116 when outer sheath 102 is disposed within a body. As will be explained in further detail below, the clear material also allows light to be transmitted down the walls of the body portion 116, exiting at the distal end 108 of the outer sheath 102 at or adjacent the surgical site. In another arrangement, at least some segments of outer sheath 102 may be constructed of an opaque biocompatible material, i.e., frosted, so as to reflect light to increase visualization within the outer sheath 102 when in use. Alternatively, all of outer sheath 102 may be constructed of an opaque biocompatible material. In one exemplary arrangement, outer sheath 102 is constructed of polycarbonate, though other biocompatible materials may be employed, including resins.

In one exemplary configuration, a navigation mechanism may be incorporated into outer sheath 102 that would permit visualization of tumors, vessels, fiber tracks, fascicles and even healthy tissue, in real-time. Indeed, as will be explained in further detail below, the navigation mechanism will enable physiological functional imaging to provide information about the characteristics of the cortical fiber tracks, thereby enabling a user to separate and park such fibers on either side of outer sheath 102 rather than cutting, stretching and potentially damaging such fibers while gaining access to a desired location within the brain. Further, as will be explained in further detail below, the navigation mechanism may also enable the surgeon to have real-time information about the fiber tract and fascicle location, after placement of outer sheath 102, and during abnormality resection procedure therethrough. In addition to white matter tract imaging, mapping of the characteristics of the cerebral blood flow may be obtained.

In one exemplary embodiment, the navigation mechanism may be an ultrasound probe (not shown) incorporated into outer sheath 102. For example, outer sheath 102 may be provided with one or more channels within the wall that defines outer sheath 102 that are configured with one or more small diameter ultrasound probes. In yet another embodiment, a low field MRI probe may be selectively placed in outer sheath 102 to provide enhanced imaging. In yet another embodiment a low field MRI imaging coil may be molded into or bonded into outer sheath 102. In still another exemplary arrangement, the probe may be an optical coherent tomography (OCT) imaging or spectroscopy. An example of the navigation mechanism may be found in commonly owned U.S. Pat. No. 9,161,820.

Distal end 108 of outer sheath 102 may include a tapered portion 120 that extends toward a center axis A-A of outer sheath 102 to a distal edge 122 that surrounds a first opening 124 in distal end 108 of outer sheath 102. Tapered portion 120 serves to ease the transition between outer sheath 102 and a distal tip portion 126 of obturator 104 (FIG. 1), without drag, trauma, or coring of tissue from a diameter that defines a body portion 128 of obturator 104 (FIG. 1) to a diameter that defines body portion 116 of the outer sheath 102. In one exemplary configuration, distal end 108 may be configured with a radius or other configuration so as to create a smooth/atraumatic transition of the brain tissue when surgical access assembly 100 is inserted into the brain.

For example, distal edge 122 is configured so as to be non-sharpened and radiused. Tapered portion 120 and distal edge 122 cooperate with obturator 104 to atraumatically move tissue, as well as various structures within the brain, including white matter, away from outer sheath 102 without cutting tissue or such structures. Indeed, unlike prior art devices that include either a blunt tip distal end or a tapered leading edge, distal edge 122 cooperates with tapered portion 120 and obturator 104 to prevent bruising and damage to various tissue. More specifically, this configuration facilitates entry of outer sheath 102 into delicate tissue, but without cutting such delicate tissue.

Body portion 116 may further be provided with a plurality of spaced apart indicators 130. Indicators 130 generally extend about the circumference of body portion 116 and each may further incorporate a secondary indicator 132 that visually illustrates a predetermined location on body portion 116, as shown in FIG. 2. Indicators 130 and 132 may be printed onto either an internal or external surface of body portion 116 with an imaging visible ink such as, for example ink containing fluro-deoxyglucose (FDG), Technicium 99, Gadolinium, titanium dust, barium sulfate, a combination of the above or other suitable imaging material. Indicators 130 and 132 provide a reference point for the operator of system 100, as structures may be visible through body portion 116. Indicator 130 and 132 may also be configured to be visible under MRI, CT, PET, or any other suitable imaging modality to enable easy identification of areas of interest. In one alternative embodiment, indicators 130 and/or 132 may be etched or printed onto body portion 116, either on the internal or external surface of body portion 116.

Figure 3:
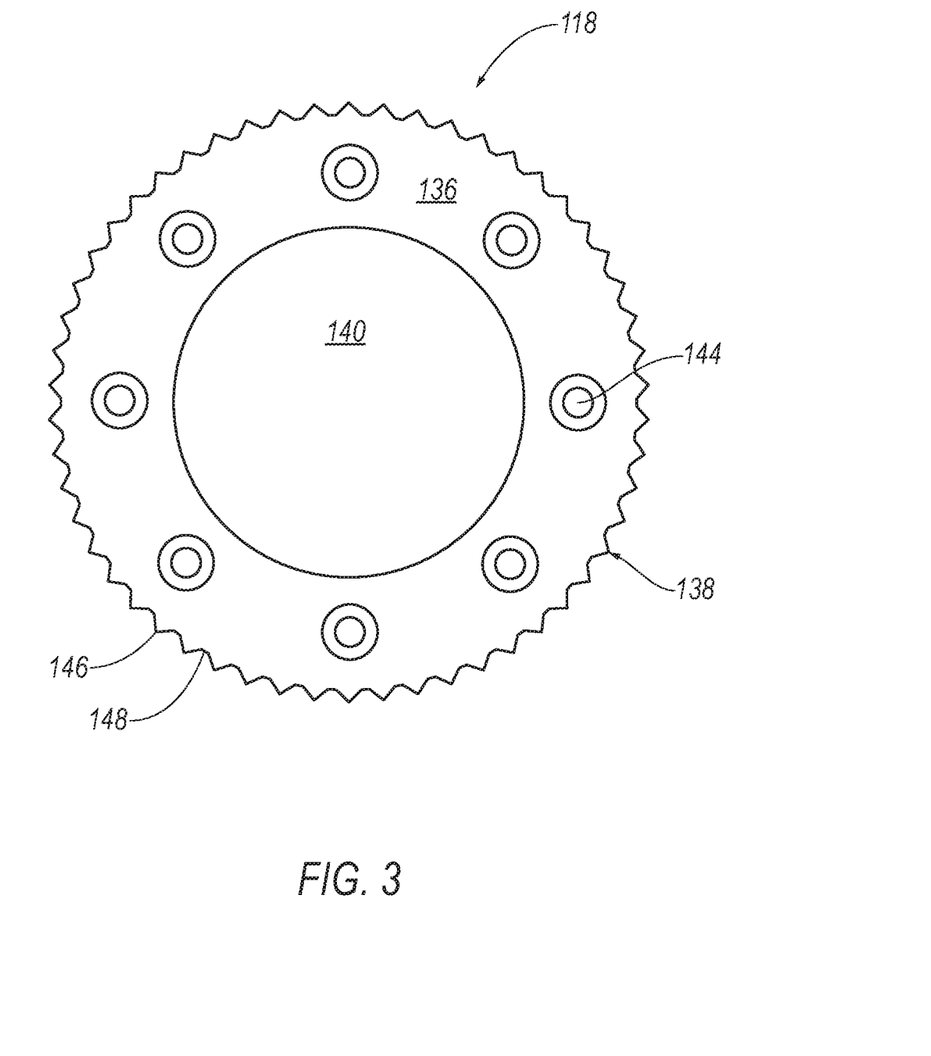
FIG. 3 is a top plan view of an outer sheath of the surgical access assembly of FIG. 1.

Details of an exemplary arrangement of grip portion 118 are best seen in FIG. 3. In one exemplary arrangement, grip portion 118 is generally configured as a flange member 136 defined by an outer periphery 138 and an inner opening 140. Inner opening 140 may be sized to generally correspond to the diameter of a lumen 142 (FIG. 2) defined by body portion 116. Outer periphery 138 is sized to have a diameter that is larger than lumen 142 of body portion 116. Flange member 136 may further be provided with one or more small openings 144 that are disposed therein. In one exemplary arrangement, a plurality of small openings 144 are provided that are spaced generally equi-distantly about inner opening 140. Outer periphery 138 may further be provided with a textured surface to provide for ease of gripping outer sheath 102. For example, in one exemplary arrangement, the textured surface comprises a plurality of alternating ridges 146 and grooves 148. However, it is understood that other textured surfaces may be employed.

Figure 4A:
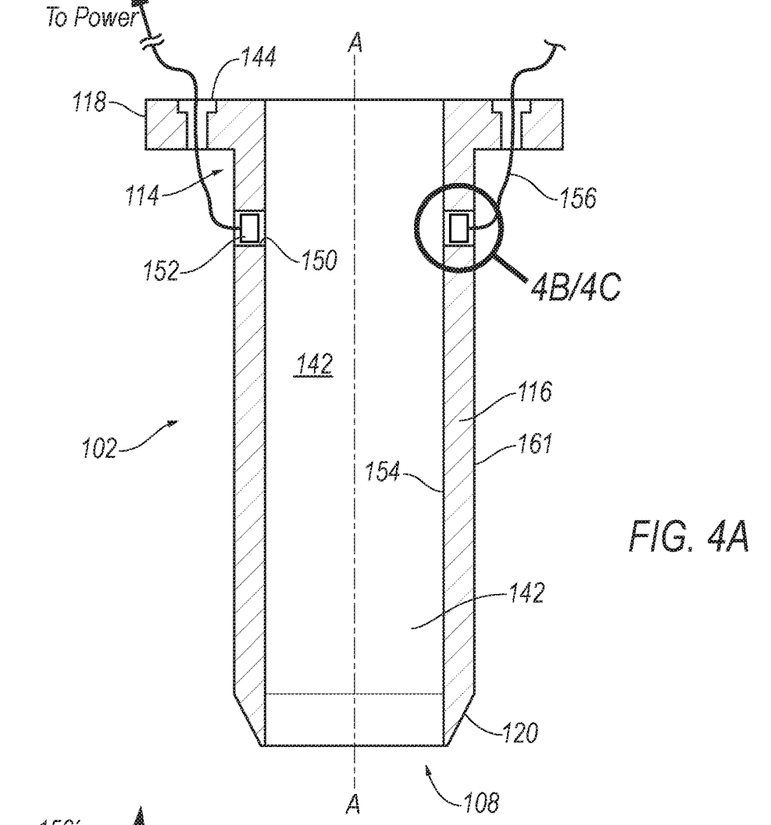
FIG. 4A is a cross-sectional view of an exemplary outer sheath for use in a surgical access assembly.

Referring now to FIG. 4A, a cross-sectional view of an exemplary arrangement of outer sheath 102 with illumination capabilities is shown. In one exemplary arrangement, outer sheath 102 defines at least one slot 150 formed closer to or adjacent to the proximal end 114. In some arrangements, outer sheath 102 defines a plurality of slots 150 adjacent to the proximal end 114, which may be spaced equi-distantly about the proximal end 114. Each of slots 150 is configured to retain at least one light source 152. In some arrangements, each light source 152 may be retained by friction fit. In other arrangements, each light source 152 may be retained by an adhesive, such as glue. Other suitable mechanisms of securing the light sources 152 within slots 150 are also contemplated. In some arrangements, each light source 152 may be placed adjacent to the distal end 108. However, placing each light source 152 adjacent to the proximal end 114 may be advantageous if the light sources 152 emit a large amount of heat because each light source 152 can therefore be positioned away from tissue, thereby preventing the light source 152 from subjecting the tissue to undesirable heating or burning.

Figure 4B:
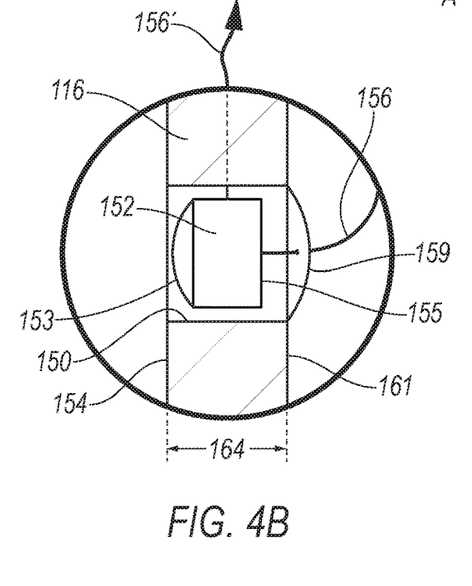
FIG. 4B is an enlarged view of encircled area 4B/4C taken from FIG. 4A in one exemplary arrangement.

Each light source 152 may be electrically connected to a remote power source (not shown). In an exemplary arrangement, each light source 152 may be electrically connected by wires 156. The wires 156 may be electrically coupled to a power end 155 of the light source 152. In one exemplary arrangement, the wires 156' may be molded into body portion 116 through thickness 164 (shown in phantom in FIG. 4B). In another exemplary arrangement, the wires 156 exit slot 150 and exit the outer sheath 102. Both arrangements prevent the wires from taking up space in the inner lumen 142. Moreover, because the light source 152 is positioned adjacent the proximal end 114, both arrangements also prevent wires from contacting tissue when the surgical assembly 100 is in use. In one exemplary arrangement, wires 156 may be directed through one of the plurality of small openings 144 of the grip portion 118, allowing wires 156 to be retained outside the outer sheath 102. To prevent the wires 156 from pulling on the light source 152, a separate end cap 159 may be pressfit otherwise secured into slot 150 on the outer surface 161 of the outer sheath 102, as shown in FIG. 4B. End cap 159 secures light source 152 within the slot 150, but may also provide an access opening (not shown) that permits the wires 156 to exit the outer sheath 102.

In one exemplary arrangement, each light source 152 is defined by an illumination end 153 and the opposite power end 155. As illustrated in FIG. 4B, in one arrangement, each light source is oriented such that the illumination end 153 is facing toward the inner lumen 142 of the body portion 116. In this manner, light emitted from each light source 152 is directed toward a central axis A-A, allowing emitted light to be reflected down the inner lumen 142 from the proximal end 114 to the distal end 108.

In some exemplary arrangements, each light source 152 may be positioned within slots 150 such that the illumination end 153 is flush with an inner surface 154 of the outer sheath 102. In one exemplary arrangement, a positioning frame (not shown) may be provided that includes a window through which the light from the light source 152 shines through. In other arrangements, as illustrated in FIG. 4B, each light source 152 may be slightly inset within slots 150 such that the illumination end 153 is positioned at least slightly inward from an inner surface 154 of body portion 116. Each light source 152 being oriented inset or flush advantageously allows an obturator, such as obturator 104 (FIG. 1) to slide smoothly along the inner surface 152 of the outer sheath 102, especially during removal of the obturator 104 from the outer sheath 102 after placement within a patient.

Figure 4C:
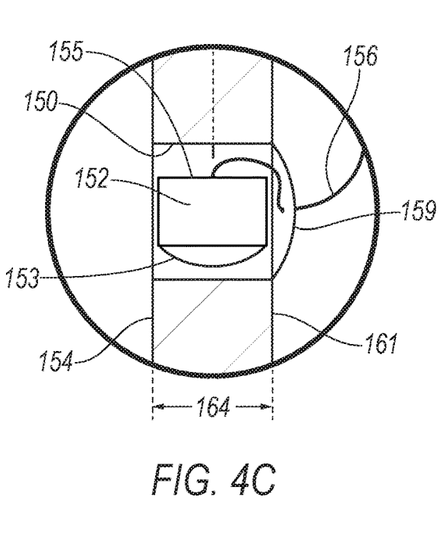
FIG. 4C is an enlarged view of encircled area 4B/4C taken from FIG. 4A in another exemplary.

In another exemplary arrangement, the light source 152 is oriented such that the illumination end 153 is oriented downwardly, as illustrated in FIG. 4C. In this arrangement, the slot 150 may be closed off at the inner surface 154 of the body portion 116. An end cap 159 may be pressfit into the slot 150 to close off the slot at outer surface 161 of the body portion 116. As with the arrangement in FIG. 4B, a small opening may be provided to allow the wires 156 to exit the outer sheath 102. This exemplary arrangement allows the light source 152 to illuminate the body portion 116 through the thickness 164 of the sidewall of the body portion 116 defined by the inner and outer surfaces, 154 and 161, respectfully. This arrangement is particularly useful for embodiments where the outer sheath 102 is constructed of clear material or even frosted, so as to reflect light.

In one exemplary arrangement, each light source 152 are LED lights, although other light devices may be utilized. LED lights are advantageous in that they do not contribute significantly to the weight of surgical access assembly 100. Moreover, LED lights can emit different combinations of colors/frequencies of light that may be incorporated in outer sheath 102, to provide improved visualization of fluorescing dyes which may be introduced into tissues to allow for the differentiation of tissues, including cancerous tissues.

Figure 5A:
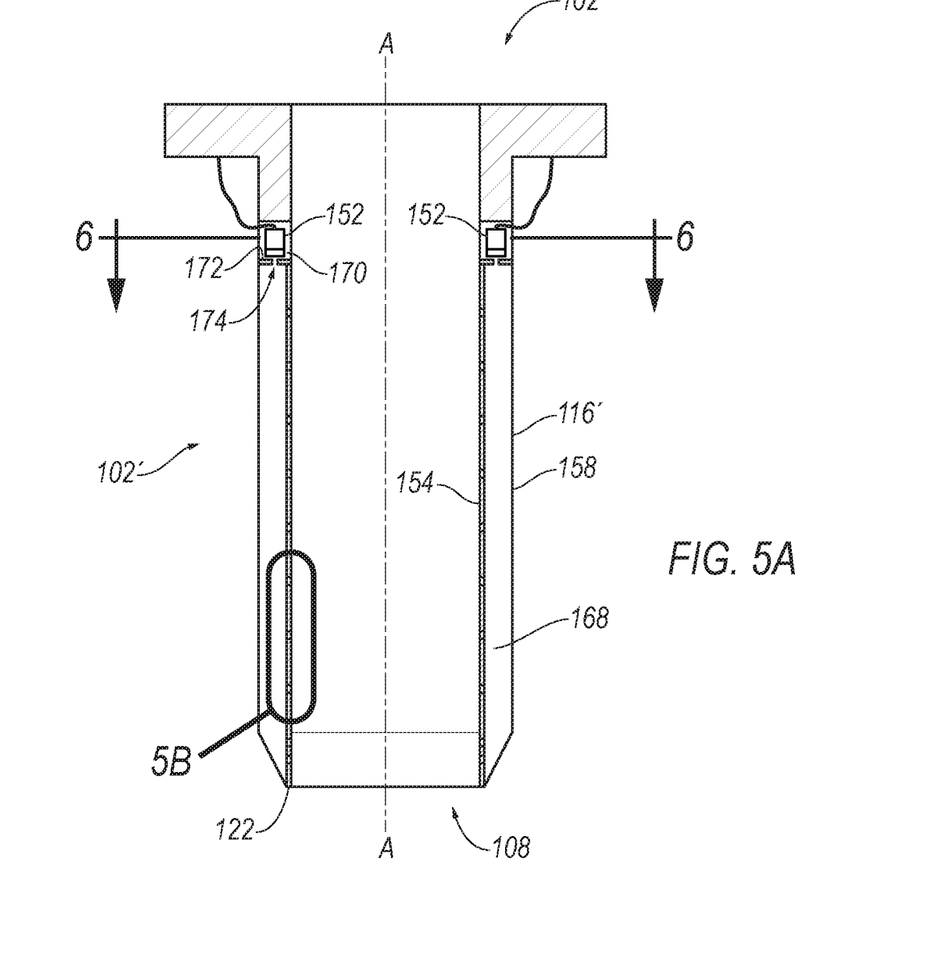
FIG. 5A is a cross-sectional view of an exemplary outer sheath for use in a surgical access assembly.
Figure 5B:
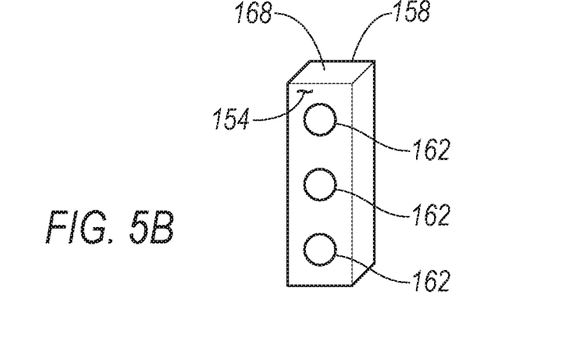
FIG. 5B is partial plan view of an inner wall surface of the outer sheath of FIG. 5A.
Figure 5C:
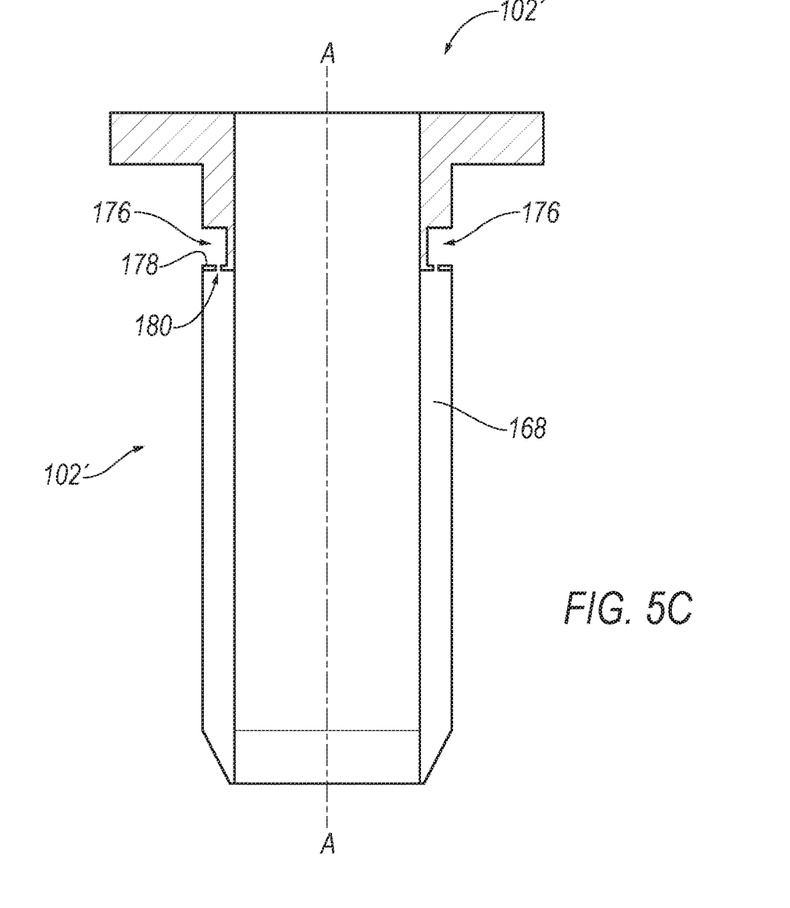
FIG. 5C is a cross-sectional view of the outer sheath of FIG. 5A.
Figure 5D:
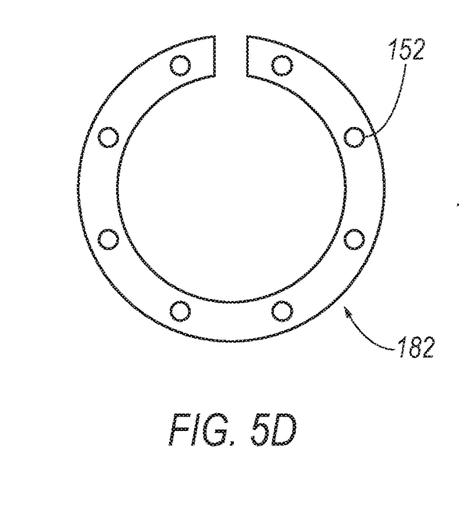
FIG. 5D is a plan view of an annular light to be used with the outer sheath of FIG. 5C.
Figure 6:
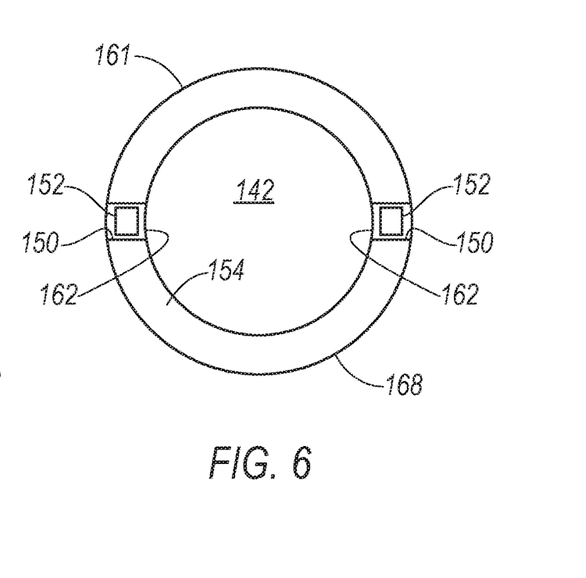
FIG. 6 is a cross-sectional view of the outer sheath of FIG. 5A, taken along lines 6-6 of FIG. 5A.

Referring now to FIGS. 5A-6, alternative arrangements of an exemplary outer sheath 102' is shown. Body portion 116' of outer sheath 102' is defined by inner surface 154 an outer surface 161. However, unlike the arrangement in FIGS. 4A-4C, the inner surface 154 and outer surface 161 are spaced apart from one another to define an annular channel 168 therebetween. With the light source 152 oriented as in FIG. 4C, the light will be directed to illuminate the entire channel 168, and thus the entire lumen 142. Annular channel 168 is closed off at the distal end 108 of outer sheath 102', forming the distal edge 122. In another exemplary arrangement, one or more channel apertures 162 may be provided through the inner surface 154 of the body portion 116'. An exemplary arrangement for channel apertures 162 is illustrated in FIG. 5B. While illustrated as being circular in shape, it is understood that channel apertures 162 may have other shapes. A channel aperture 162 may be positioned anywhere along the length of the inner surface 154, with the channel aperture 162 being in communication with the annular channel 168. Thus, when light from the light source 152 is directed down through the annular channel, light may also be able to shine directly through the channel apertures 162. To provide a smooth sliding surface, the channel aperture 162 may be closed by a window material that still allows light to escape therethrough. In another exemplary arrangement, a plurality of channel apertures 162 are spaced apart longitudinally along the length of the outer sheath 116, and/or radially about axis A-A, allowing light from the light source 152 to be delivered to lumen 142 all along the length of the body portion 116'.

In one arrangement, body portion 116' further includes a single annular channel aperture 162 extending from inner surface 154 to single annular channel 168. In this arrangement, the single annular channel aperture 162 may be located adjacent to distal end 108 of outer sheath 102' in order to deliver light to increase visualization within outer sheath 102' at the distal end 108 and adjacent the surgical site, but without delivery of heat that may be generated by the light source.

The light source 152 may be disposed in a light chamber 170 formed adjacent the proximal end 114. The light chamber 170 may include a floor member 172 to prevent the light source 152 from falling into the annular channel 168. In one exemplary arrangement the floor 172 is constructed of a clear material to permit light from the light source to pass therethrough. Alternatively, the floor 172 may be provided with a small opening 174 that permits light to pass therethrough.

In a further exemplary arrangement, as shown in FIG. 5C, the outer sheath 102 may be provided with a mounting notch 176 positioned adjacent the proximal end 114. In one iteration, disposed through a bottom section 178 is a window or opening 180. The window or opening 180 is directed to be in communication with the annular channel 168. Alternatively, no annular channel 168 may be provided and the notch 176 allows for alignment of a light source through the thickness 164 of the outer sheath 102. An annular light ring 182 (FIG. 5D) may be disposed within the mounting notch 176. The light ring 182 may carry a number of light sources 152 therein. Moreover, the position of the light sources may correspond with openings 144 formed through the grip ring 118. To facilitate mounting of the annular light ring 182, in one exemplary arrangement, the annular light ring 182 may be constructed as a split ring allowing the annular light ring 182 to flex when mounting and to snap into place within the mounting notch 176.

Figure 7:
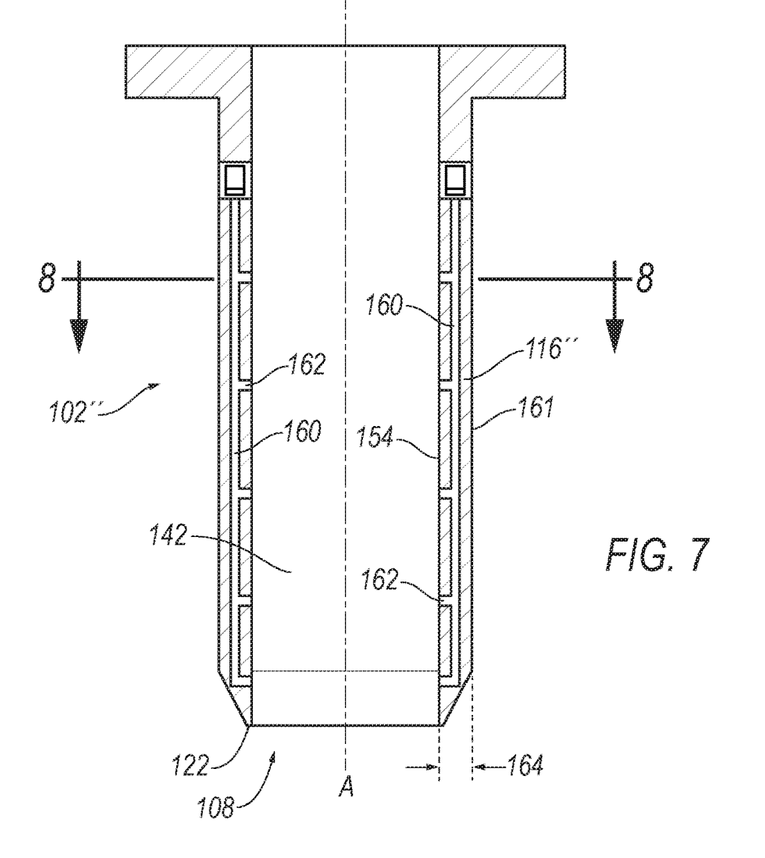
FIG. 7 is a cross-sectional view of an outer sheath for use in a surgical access assembly.
Figure 8:
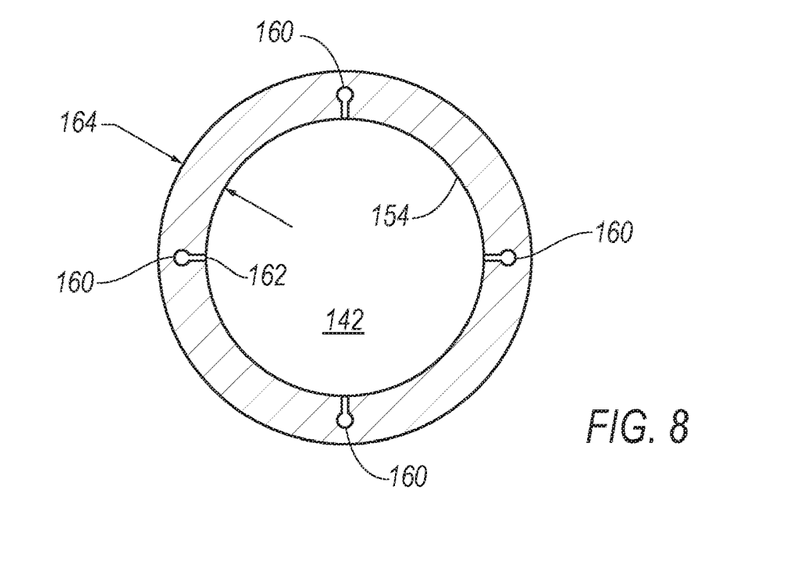
FIG. 8 is a cross-sectional view of the outer sheath of FIG. 7, taken along lines 8-8 of FIG. 7.

Referring now to FIGS. 7 and 8, another exemplary arrangement of an outer sheath 102" is shown. Body portion 116" of outer sheath 102" is similar to outer sheath 102 in that the outer surface 161 and inner surface 154 define a thickness 164 of body portion 116". Disposed within the thickness 164 of body portion 116" are axially extending channels 160. Thickness 164 may provide more rigidity and support for outer sheath 102" than outer sheath 102'. Body portion 116" further includes one or more annular channel apertures 162 extending from the inner surface 154 to each of the plurality of axial channels 160 so as to be in communication with each of the plurality of axial channels 160. The plurality of annular channel apertures 162 are placed along the outer sheath 102 about the A-A axis, allowing for light to be delivered downward from the proximally located light sources 152 and to illuminate the lumen 142.

The axial channels 160 either terminate short of the distal end 108 or are closed off at the distal end 108 of outer sheath 102", forming the distal edge 122. The light source 152 is oriented as in FIG. 4C, so as to direct light down the channel toward the distal end 108. In this arrangement, the plurality of annular channel apertures 162 allow light from light source 152 to be delivered both through the sidewall of the body portion 116 and directly to lumen 142.

In one arrangement, each of the axial channels 160 includes only one annular channel aperture 160 located adjacent to the distal end 108 of outer sheath 102" in order to deliver light down toward the distal end 108 of the outer sheath 102", thereby increasing visualization at the surgical site.

Figure 9:
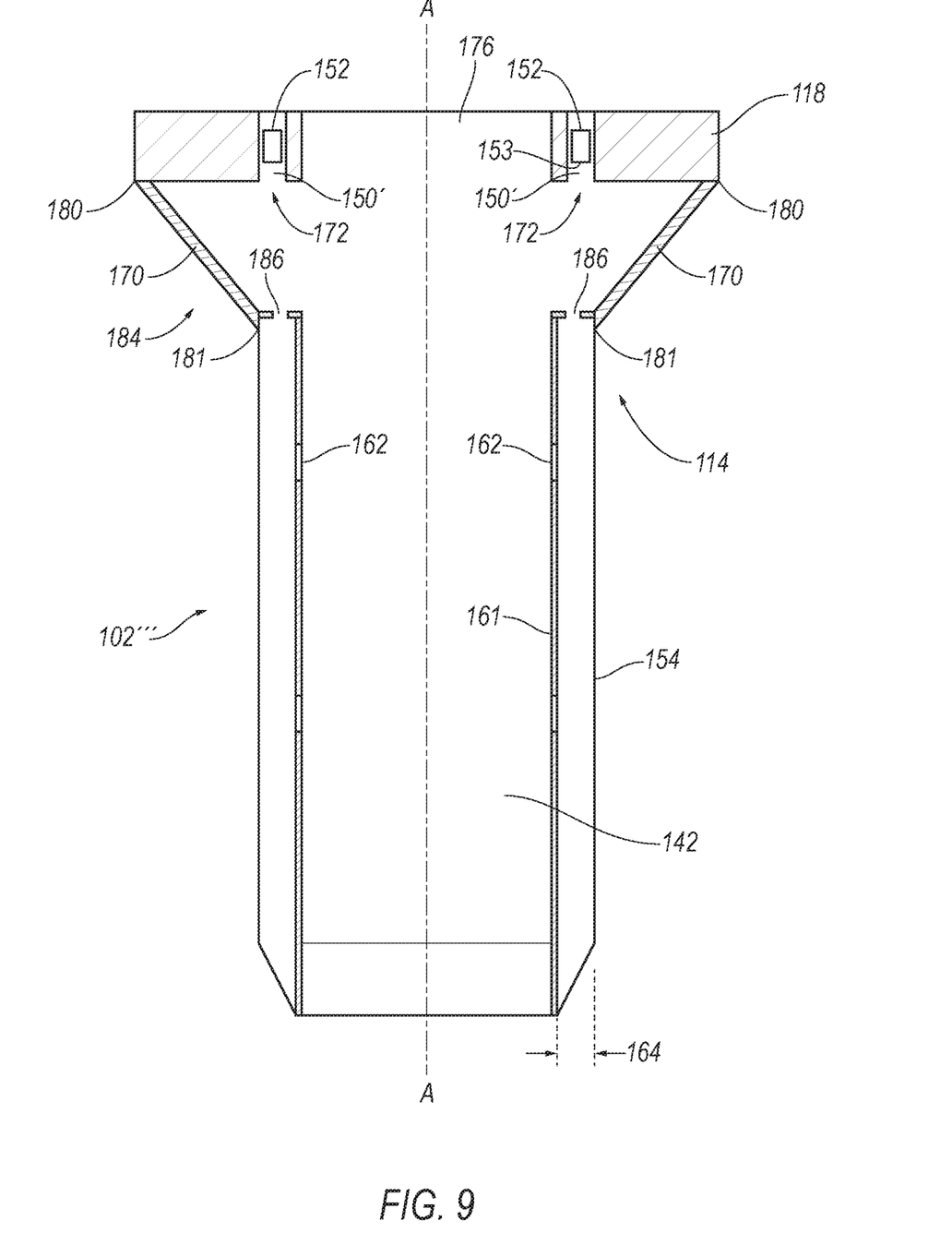
FIG. 9 is a cross-sectional view of exemplary outer sheath for use in a surgical access assembly.

A further exemplary arrangement of an outer sheath 102''' is shown in FIG. 9. This arrangement is similar to that shown in FIGS. 4A and 5A, in that the outer sheath 102''' includes a body portion 116 and a grip portion 118. In addition, outer sheath 102''' further comprises a transition section 170. The transition section 170 is disposed between the body portion 116 and the grip portion 118 and serves to support the grip portion 118. The transition section 170 has a first end 180 connected to the grip portion 118 and a second end 181 connected to the proximal end 114 of the body portion 116. In some arrangements, the transition section 170 is defined by a tapered portion 184 extending inwardly from the first end 180 at the radially extending portion 174 toward the central axis A-A such that a second end 178 is connected to the proximal end 114 of the body portion 116. The grip portion 118 further includes a mounting portion 172 that includes slots 151' therein. The slots 151' receive light sources 152 therein such that the light is oriented toward the distal end 108 of the body portion 116. Mounting portion 172 further defines a mounting portion opening 176, which has a diameter generally corresponding to, and aligned with, the diameter of the lumen 142. The mounting portion opening 176 allows an obturator, such as obturator 104, to be slidingly engaged with the outer sheath 104 when positioning the obturator 102 and outer sheath 104 in an introducing configuration, or to facilitate removal of the obturator 102 from the outer sheath 104 when the outer sheath 102 is positioned within a patient.

In this configuration, mounting portion 172 may retain at least one light source 152. In another arrangement, the light sources are disposed radially around the axis A-A within a plurality of slots 151' formed in the mounting portion 172. In one exemplary arrangement, the at least one light source 152 is positioned such that the illumination end 153 is oriented downwardly. A small radially extending portion opening (not shown) may be provided to allow the wires 156 to exit the top of the outer sheath 102, away from tissue and the working space within the outer sheath 102. The light source 152 may be positioned to direct light at the thickness of the body portion 116 of the outer sheath 104. This exemplary arrangement allows the light source 152 to illuminate the body portion 116 through the thickness 164 of the sidewall defined by the inner and outer surfaces, 154 and 161, respectfully. This arrangement is particularly useful for embodiments where the outer sheath 102 is constructed of clear material or even frosted, so as to reflect light.

In one exemplary arrangement, the transition section 170 may further include a transition-section opening 186 defined on an inside surface 188 of the transition section 170. The transition-section opening 186 may align with light source 152, allowing light to enter the transition-section opening 186.

In some arrangements, transition-section opening 186 is in communication with an annular channel between the inner and outer surfaces 154 and 161, respectively, similar to the arrangement shown and described in connection with FIGS. 5A and 6. In other arrangements, transition-section opening 186 is in communication with at least one of a plurality of channels between the inner and outer surfaces 154 and 161, respectively, similar to the arrangement shown and described in connection with FIGS. 7 and 8.

In some arrangements, the outer sheath 102''' may include one or more channel apertures 162, as also described in connection with FIGS. 5A and 8. The one or more channel apertures 162 may be positioned anywhere along the length of the inner surface 154, with the one or more channel apertures being in communication with the single channel or the plurality of channels between the inner and outer surface 154 and 161, respectively.

Figure 10:
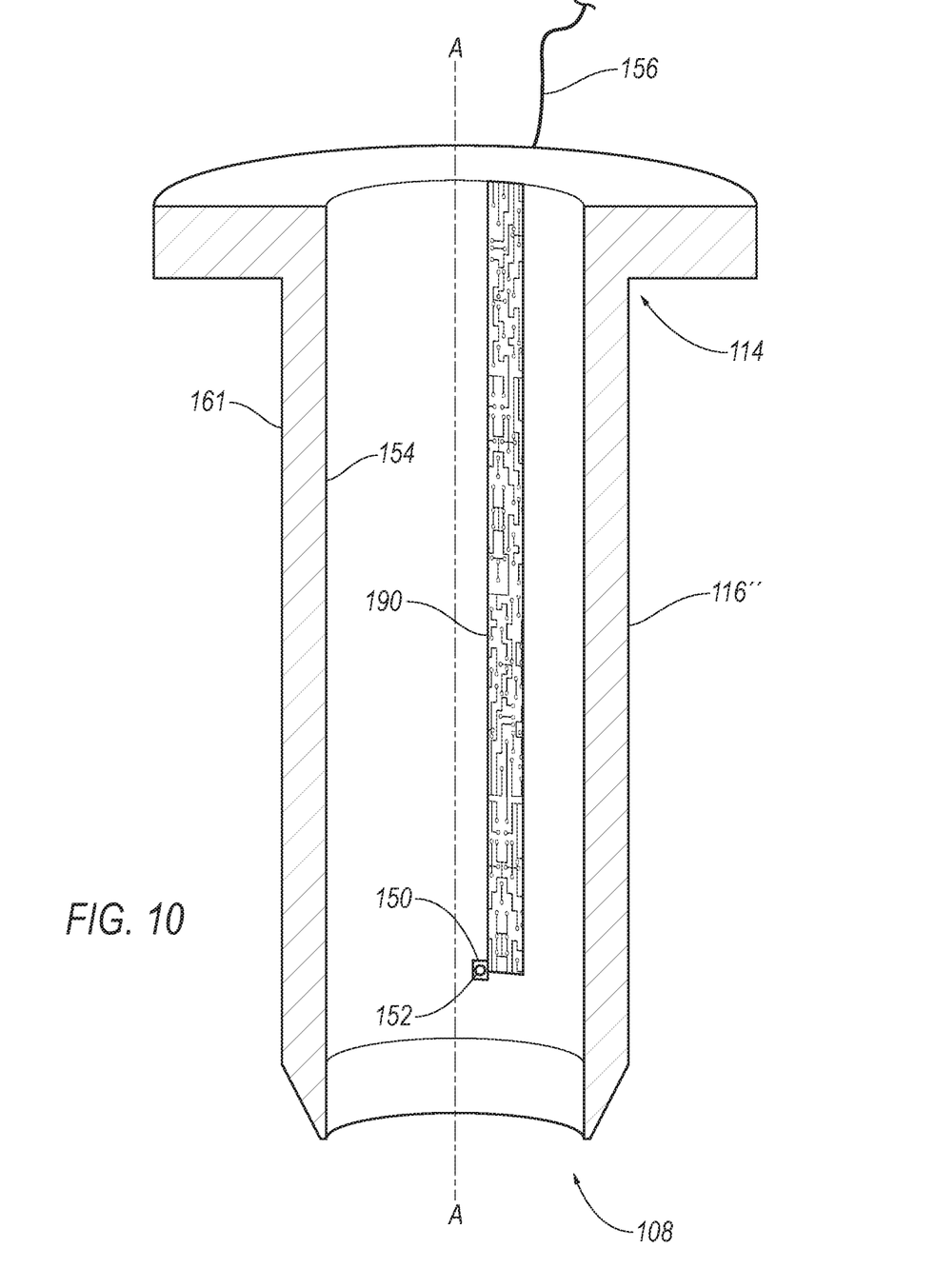
FIG. 10 is a cross-section view of an exemplary outer sheath for use in a surgical access system.

Referring now to FIG. 10, a further exemplary arrangement of an outer sheath 102'''' is shown. Body portion 116'' of other sheath 102'''' is defined by inner surface 154 and outer surface 161. This arrangement is similar to that shown in FIGS. 4A and 5A, in that the outer sheath 102'''' includes a body portion 116'' and has one or more slots 150 formed through the wall thickness 164.

Each slot 150 (shown disposed adjacent distal end 108) may retain at least one light source 152 electrically connected to a remote power source (not shown). In some arrangements, each light source 152 may be electrically connected to the remote power source by a printed circuit board (PCB) 190 connected to a single wire 156. Electrically connecting each light source 152 to the remote power source via the PCB 190, which may be connected to a single wire 156, is advantageous because it reduces the number of wires, thus decreasing interference of wires with surgical access assembly 100. PCB 190 may be a flexible PCB. For example, the PCB 190 may be a flex circuit screen printed on polyester. In one exemplary arrangement, the PCB 190 may be located on the grip portion 118. In another exemplary arrangement, the PCB 190 may be located on the inner surface 154 of the body portion 116''. In the arrangements where the PCB 190 is located on the inner surface 154 of the body portion 116'', the obturator 104 can still be slidingly engaged with the outer sheath 102 without interference from the PCB 190.

In the arrangement shown, the body portion 116'' includes at least one slot 150 spaced proximally to the distal end 108 of outer sheath 102''''. The at least one slot 150 may be placed anywhere along the A-A axis so long as the at least one slot 150 is spaced apart from the distal end 108 to avoid the transmission of any heat to brain tissue located at the distal end 108. It should be noted that current draw may be affected depending on where the at least one slot 150 is located on the body portion 116''. For example, there is a lower current draw if the at least one slot 150 is located closer to the distal end 108. This is because the light source 152 is closer to the body tissue near the distal end 108, so there is a need for less intensity of light. This is advantageous because less power is sent to illuminate the light source 152, and thus less heat is generated at the light source 152.

It will be appreciated that the surgical access system described herein has broad applications. The foregoing embodiments were chosen and described in order to illustrate principles of the apparatuses as well as some practical applications. The preceding description enables others skilled in the art to utilize apparatuses in various embodiments and with various modifications as are suited to the particular use contemplated. In accordance with the provisions of the patent statutes, the principles and modes of operation of this disclosure have been explained and illustrated in exemplary embodiments.

It is intended that the scope of the present apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the disclosure should be determined, not with reference to the above description, but should instead be determined with reference to the appended claims, along with the full scope of equivalents to which such claims are entitled. It is anticipated and intended that future developments will occur in the arts discussed herein, and that the disclosed systems will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the apparatus within the scope of these claims and their equivalents be covered thereby. In sum, it should be understood that the invention is capable of modification and variation and is limited only by the following claims.

What is claimed is:

1. An outer sheath with integrated illumination for a surgical access assembly, comprising:
   a proximal end defining a first opening;
   a distal end opposite the proximal end, the distal end defining a second opening;
   a hollow body portion positioned between the proximal end and the distal end and defining a passageway, the body portion including at least one slot formed therein, the at least one slot retaining at least one light source adjacent the proximal end, and
   a grip portion disposed around the first opening, wherein the grip portion includes a plurality of small openings configured to direct at least one wire connected to the at least one light source.

2. The outer sheath of claim 1, wherein the at least one light source is an LED light element.

3. The outer sheath of claim 2, wherein the at least one LED light element is inset within the slot so as to be positioned inwardly from an inner surface of the body portion.

4. The outer sheath of claim 1, wherein the light source is defined by an illumination end and wherein the illumination end is oriented toward the passageway.

5. The outer sheath of claim 1, wherein the light source is defined by an illumination end and wherein the illumination end is oriented downward.

6. The outer sheath of claim 1, wherein the light source is operatively connected to a power source by a wired connection and wherein the wired connection orients wires external to the body portion.

7. The outer sheath of claim 1, wherein at least one segment of the body portion is frosted.

8. The outer sheath of claim 1, wherein the body portion is defined by an outer surface and an inner surface spaced from the outer surface to define an annular channel therebetween, and wherein the light source is directed into the annular channel.

9. The outer sheath of claim 8, wherein the body portion further includes at least one aperture extending through the inner surface of the body portion to provide communication between the annular channel and the passageway.

10. The outer sheath of claim 9, wherein the light source is oriented downward to deliver light to the annular channel.

11. The outer sheath of claim 1, wherein the slot is formed as an annular notch.

12. The outer sheath of claim 11, wherein the light source is an annular ring having a plurality of lights therein, oriented downward.

13. An outer sheath with integrated illumination for a surgical access assembly, comprising:
   a proximal end defining a first opening;
   a distal end opposite the proximal end, the distal end defining a second opening;
   a hollow body portion positioned between the proximal end and the distal end, the hollow body portion defining a lumen therethrough, the body portion defined by an outside surface and an inside surface;
   a grip portion disposed around the first opening and including a mounting flange,
   a transition section extending between the grip portion and the body portion, the transition section having a first end connected to the grip portion and a second end connected to the proximal end; and
   wherein the mounting flange includes at least one light element mounted therein and oriented downward to illuminate the lumen, and
   wherein the grip portion includes a plurality of small openings configured to direct at least one wire connected to the at least one light element.

14. The outer sheath of claim 13, wherein the at least one light element is oriented toward a thickness of the body portion that is defined by the outside surface and the inside surface.

15. The outer sheath of claim 13, wherein at least one channel is formed between the outside surface and the inside surface, and wherein the inside surface includes at least one aperture that is communication with the at least one channel.

16. The outer sheath of claim 14, wherein the body portion is defined by a plurality of channels between the outside surface and the inside surface.

17. The outer sheath of claim 15, wherein the transition section includes at least one transition-section opening defined on an inside surface of the transition section, the transition-section opening aligned with the light element.

18. The illuminated outer sheath of claim 15, wherein the at least one light element is an LED light.

19. The outer sheath of claim 15, wherein at least one segment of the hollow body portion is frosted.

20. An outer sheath with integrated illumination for a surgical access assembly, comprising:
   a proximal end defining a first opening;
   a distal end opposite the proximal end, the distal end defining a second opening; and
   a body portion positioned between the proximal end and the distal end, the body portion including:
      at least one slot formed therein, the at least one slot retaining at least one light,
      a grip portion disposed around the first opening, wherein the grip portion includes a plurality of small openings configured to direct at least one wire connected to the at least one light,
      and
      a printed circuit board disposed on an inner surface of the body portion, the printed circuit board extending from the proximal end and spaced apart from the distal end, the printed circuit board electrically connected to the at least one light.

* * * * *